United States Patent [19]

Haworth

[11] Patent Number: 5,012,668

[45] Date of Patent: May 7, 1991

[54] INCLINED ELECTRODE SURFACE ACOUSTIC WAVE SUBSTANCE SENSOR

[75] Inventor: John Haworth, Lynnwood, Wash.

[73] Assignee: The Boeing Company, Seattle, Wash.

[21] Appl. No.: 397,009

[22] Filed: Aug. 22, 1989

[51] Int. Cl.$^5$ ............................................. G01N 31/00
[52] U.S. Cl. .................................. 73/24.06; 310/313 B
[58] Field of Search ............................ 73/23, 24, 599; 310/313 R, 313 B, 313 D; 422/68, 69, 98

[56] References Cited

U.S. PATENT DOCUMENTS

| | | | |
|---|---|---|---|
| 3,828,607 | 8/1974 | Janzen et al. | 73/23 |
| 3,845,419 | 10/1974 | Nudd | 310/313 B |
| 4,100,811 | 7/1978 | Cullen et al. | 310/313 B |
| 4,193,045 | 3/1980 | Houkawa et al. | 310/313 R |
| 4,312,228 | 1/1982 | Wohltjen | 73/23 |
| 4,633,117 | 12/1986 | Bloch et al. | 310/313 B |
| 4,895,017 | 1/1990 | Pyke et al. | 73/23 |
| 4,912,356 | 3/1990 | Mariani et al. | 310/313 B |

OTHER PUBLICATIONS

Thomson-CSF Brochure, Section I through III.5.
Lewis et al., "Recent Developments in SAW Devices," *IEEE Proceedings*, vol. 131, Pt. A., No. 4, pp. 186–215; Jun. 1984.
Potter et al., "Surface Acoustic Wave Slanted Device Technology," *IEEE Transactions on Sonics and Ultrasonics*, vol. SU-26, No. 6, pp. 411–418, Nov. 1979.

*Primary Examiner*—John E. Chapman
*Assistant Examiner*—Rose M. Finley
*Attorney, Agent, or Firm*—Christensen, O'Connor, Johnson & Kindness

[57] ABSTRACT

A chemical sensor for detecting a plurality of different chemical substances. A chemical sensor (100, 200) includes a substance sensitive SAW device (102, 202) and a reference SAW device (104, 204) formed on the same substrate (106). A plurality of interlaced fingers (112 and 114, 120 and 122; or 206 and 208, and 210 and 212) extend outwardly from the inclined source and output electrodes in parallel relationship with reach other. An RF pulse signal is applied to the inclined source electrodes in both the substance sensitive and reference SAW devices, causing surface acoustic waves to be generated that propagate perpendicularly away from the interlaced fingers toward the inclined output electrodes. A plurality of polymer coatings are applied in regions between the inclined source and output electrodes so that the surface acoustic waves generated by successive overlapped interlaced fingers propagate through different regions and coatings. In the substance sensitive SAW device, each polymer coating has a characteristic affinity to absorb a different chemical substance or substances, such absorption changing the phase, delay, and amplitude of a surface acoustic wave propagating through the region in which the coating is applied. In the reference SAW device, corresponding coatings are applied that do not absorb any of the chemical substances. Time multiplexed output signals from the substance sensitive SAW device and reference SAW device are compared in a mixer (134) to determine the differences in phase or delay, and in a differential amplifier (150), to determine differences in amplitude of the surface acoustic waves passing through corresponding regions.

21 Claims, 4 Drawing Sheets

5,012,668

INCLINED ELECTRODE SURFACE ACOUSTIC WAVE SUBSTANCE SENSOR

TECHNICAL FIELD

This invention generally pertains to surface acoustic wave (SAW) devices, and particularly relates to a chemical sensor SAW device in which a characteristic parameter of a surface acoustic wave propagating through the device changes when the SAW device is exposed to a particular chemical substance.

BACKGROUND OF THE INVENTION

A SAW device typically comprises two sets of interdigital electrodes, formed at opposite ends on a surface of a piezoelectric crystal or other suitable substrate. Conventional photolithographic and etching techniques are used to produce the electrode pattern. When a radio frequency (RF) voltage is applied to the electrode pair on one end of the device, a Rayleigh surface acoustic wave is generated that propagates over the substrate, toward the other pair of electrodes, on which is developed a corresponding RF voltage. Since the surface acoustic wave propagates by mechanical deformation of the crystal and structure in the region between the pairs of electrodes, any material applied as a coating on that region of the substrate can affect certain characteristic parameters of the surface acoustic wave, such as its amplitude, velocity, and phase. Furthermore, when the material is exposed to a chemical substance, e.g., a vapor, these parameters change as the chemical substance is absorbed by the material coating the substrate. The change in mass of the coating resulting from its absorption of the chemical substance causes a proportional change in the phase of the RF signal output from the electrodes that are excited by the surface acoustic wave. Similarly, the amplitudes of the surface acoustic wave and of the output signal change in proportion to the amount of the chemical substance that is absorbed, although the sensitivity of the device to such change with respect to amplitude of the output signal is much less than with respect to frequency.

By selecting the material coating applied to the substrate, which is typically an organic polymer, for its characteristic solubility in a desired chemical substance, the SAW device can be used to detect that specific chemical substance. Since other operating parameters, such as ambient temperature, may effect the signal output from the chemical sensor SAW device, it is preferable to compare a signal output from a reference SAW device formed on the same substrate (but coated with a material that does *not* absorb chemical substances). Since both the reference and chemical sensor SAW devices are exposed to the same environment, any difference between their output signals is indicative of absorption of a chemical substance by the one SAW device.

SAW devices used for detecting chemical substances in the manner described above are known in the art, as exemplified by the disclosure of U.S. Pat. No. 4,312,228. Such devices are commercially available from a company that pioneered their early development, Microsensors Systems, Inc., Fairfax, Va. To construct a chemical detector that can sense more than one substance using presently available SAW devices, a plurality of SAW sensors are normally employed, each sensor including a different organic polymer coating selected for its solubility in a different chemical substance or group of chemical substances. Detection of a specific chemical substance is effected by analyzing the signals produced by the plurality of different SAW devices when exposed to an unknown substance, matching the pattern of responses from all the sensors to a set of known patterns. Prior art SAW chemical sensors have generally relied only on the change in the frequency of the output signal, when exposed to an unknown substance, and not on changes in amplitude. As the number of different chemical substances of interest increases, so does the required number of different SAW sensors needed to identify a particular substance from the variety of substances that might be present. For certain applications, the cost and complexity of such a chemical substance detector may be excessive.

In consideration of the preceding problem, it is an object of the present invention to provide a SAW sensor for detecting a plurality of different chemical substances. A further object is to provide a SAW sensor in which both a frequency change and an amplitude change in the output signal, resulting from exposure of the sensor to a chemical substance is used in detecting and identifying the substance. Yet a further object is to provide a SAW sensor in which a range of surface acoustic wave frequencies are generated to detect different chemical substances, where the sensitivity of the material coatings on the sensor to different chemical substances varies and the range of frequencies applied to a specific material coating is selected to compensate for the variation in sensitivity. Still a further object is to minimize errors in determining changes in phase in the SAW sensor when it is exposed to a chemical substance, where such errors result from phase ambiguity. These and other objects and advantages of the invention will be apparent from the attached drawings and the Description of the Preferred Embodiments that follow.

SUMMARY OF THE INVENTION

In accordance with the present invention, a surface acoustic wave sensor for detecting a substance includes a first and a second pair of electrodes formed on the surface of a substrate, each pair including a plurality of spaced apart, generally parallel interlaced fingers extending from one electrode of the pair to the other electrode of the pair. One end of each of the second pair of electrodes is substantially closer to the first pair of electrodes than an opposite end thereof. The interlaced fingers of the second pair of electrodes are generally parallel to those of the first pair of electrodes. Due to the disposition of the first and second pair of electrodes on the substrate, the extent of overlap between any interlaced finger and successive interlaced fingers of the first and second electrode varies along the length of the electrodes. A plurality of different coatings are disposed on generally adjacent patches on the substrate, in an area between the first and second pair of electrodes. These coatings are operative to change the phase, delay, and amplitude of a surface acoustic wave propagating over the substrate between overlapping interlaced fingers of the first and second electrodes, as a function of the amount of the substance absorbed by the coating comprising the region through which the surface acoustic wave passes.

In one form of the surface acoustic wave sensor, the spacing between successive adjacent interlaced fingers is substantially constant for both the first pair of electrodes and the second pair. In another form of the surface acoustic wave sensor, the spacing between successive adjacent interlaced fingers varies between the proximal ends and distal ends of the first and second electrodes. As a result, the frequency of the surface acoustic wave propagating over the substrate also varies between the proximal and distal ends of the first and second electrodes. Where the spacing between adjacent interlaced fingers is greater at the proximal ends of the first and second electrodes than at their distal ends, a coating that is disposed between the proximal ends of the electrodes is exposed to a lower frequency surface acoustic wave than is a coating disposed between the distal ends of the first and second electrodes. In response to the surface acoustic wave, the second pair of electrodes produces an output signal.

The surface acoustic wave sensor may also comprise a reference surface acoustic wave device, which includes a third and fourth pair of electrodes, each pair having a plurality of spaced apart, generally parallel interlaced fingers extending from one electrode of the pair toward the other. The third and fourth pairs of electrodes are spaced apart from each other, with one end of each of the fourth pair of electrodes being substantially closer to the third pair of electrodes than an opposite end thereof. The extent of overlap between any interlaced fingers and successive interlaced fingers on the third and fourth pairs of electrodes varies along the length of the electrodes. A nonabsorptive coating is disposed on the substrate, in an area between the third and fourth pairs of electrodes. The nonabsorptive coating is substantially unaffected by the substances absorbed by the coatings between the first and second pair of electrodes, so that the phase, delay, and amplitude of a surface acoustic wave propagating over the substrate between overlapping fingers of the third and fourth pair of electrodes is not affected by such substances. A reference signal is output from the fourth pair of electrodes for comparison to the signal output from the second pair of electrodes, compensating for changes due to temperature.

Impulse signal means are connected to the first pair of electrodes and are operative to apply a periodically varying voltage signal to the first pair of electrodes that excite the surface acoustic wave. Analysis means are connected to receive the signal output from the second pair of electrodes and are operative to monitor the change in amplitude and either the phase shift or the delay of the surface acoustic wave caused by the absorption of a substance by any of the plurality of coatings.

Another aspect of the present invention is drawn to a method for sensing and identifying one or more of a plurality of different substances, including steps that are generally consistent with the functions of the apparatus described above. The method further provides for identifying a substance absorbed by one or more of the plurality of coatings as a function of a time dependent sense signal and as a function of a change in the signal that is caused by such absorption.

DESCRIPTION OF THE PREFERRED EMBODIMENTS

Figure 1:
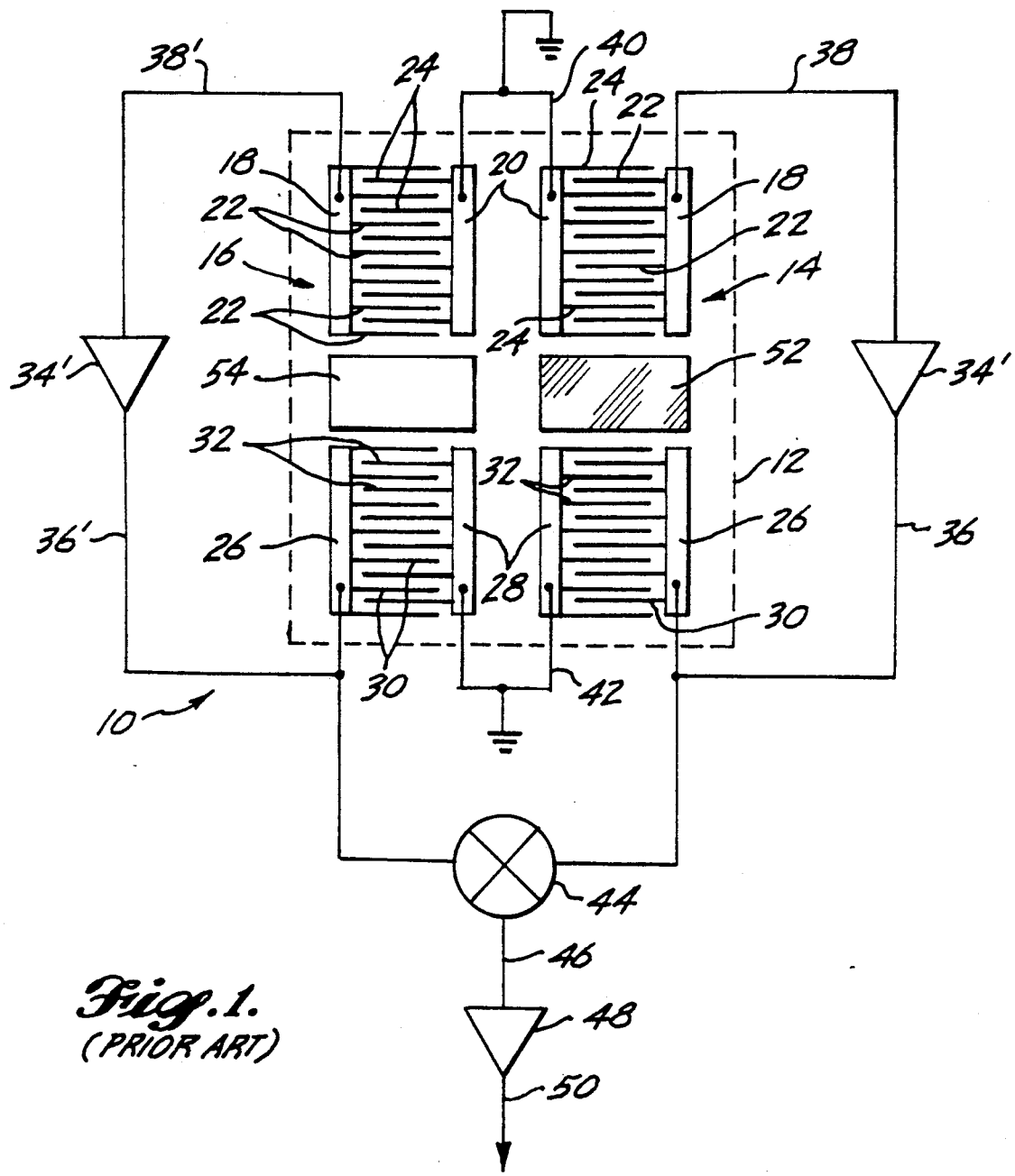
FIG. 1 is a schematic block diagram of a prior art SAW chemical sensor.

In FIG. 1, a prior art chemical sensor 10 includes a piezoelectric substrate 12, on which are disposed a substance sensitive SAW device 14 and a reference SAW device 16. Both substance sensitive SAW device 14 and reference SAW device 16 include a first pair of generally parallel electrodes 18 and 20 and a second pair of generally parallel electrodes 26 and 28. Between electrodes 18 and 20 are disposed a plurality of interlaced fingers 22 and 24, interlaced fingers 22 extending outwardly from electrodes 18 toward electrodes 20, and interlaced fingers 24 extending outwardly from electrodes 20 toward electrodes 18, in generally parallel relationship to interlaced fingers 22. As implied by their name, interlaced fingers 22 and 24 are formed on piezoelectric substrate 12 in alternating relationship with one another. Similarly, interlaced fingers 30 extend outwardly from electrodes 26 toward electrodes 28 and interlaced fingers 32 extend outwardly from electrodes 28 toward electrodes 26. The extent of overlap between all of interlaced fingers 22 and 24 and between all of interlaced fingers 30 and 32 is generally uniform in both substance sensitive SAW device 14 and reference SAW device 16.

The output from a radio frequency (RF) amplifier 34 is connected by a lead 36 to electrode 26 on substance sensitive SAW device 14, while the input to the RF amplifier is connected by a lead 38 to electrode 18 on that SAW device. Leads 40 and 42 respectively connect each of the electrodes 20 and 28 to ground. If the gain of RF amplifier 34 is greater than the signal loss through substance sensitive SAW device 14, and if the phase of a signal at the input to the RF amplifier provides positive feedback relative to its output, oscillations are maintained through substance sensitive SAW device 14 at a frequency dependent upon the spacing of interlaced fingers 30 and 32 and the propagation delay between the first pair of electrodes 18 and 20 and the second pair of electrodes 26 and 28. Surface acoustic waves are generated in a beam approximately as wide as the overlapping portions of interlaced fingers 22 and 24 and interlaced fingers 30 and 32 in substance sensitive SAW device 14. The surface acoustic waves propagate from the region between electrodes 26 and 28, along the surface of piezoelectric substrate 12, and into the region between electrodes 18 and 20 on the device. Interlaced electrodes 22 and 24 detect the surface acoustic wave in substance sensitive SAW device 14, producing an output signal which is input to RF amplifier 34 over lead 38. Assuming that the conditions for oscillation are met, the surface acoustic waves continue to propagate through the device as described above.

Interposed between interlaced fingers 30/32 and interlaced fingers 22/24 is a substance sensitive region 52, comprising a thin coating of a material that is selected to absorb a particular chemical substance or group of chemical substances. Typically, an organic polymer, such as fluoropolyol or polyethylene maleate, is selected for application to region 52. When exposed to the chemical substance or substances of interest, the polymer absorbs the substance, so that its mass increases. Since region 52 is interposed in the path of the surface acoustic waves that are propagating between the overlapping portions of interlaced fingers 30 and 32 and interlaced fingers 22 and 24, the mass of the polymer coating affects the phase and amplitude of the surface acoustic waves. As a result, absorption of the chemical substances or substances by the coating at region 52 causes a change in the phase and amplitude of the surface acoustic wave signal, and the frequency of the corresponding feedback signal on lead 36. Analysis of this signal could enable the device to detect the desired chemical substance or substances.

Since environmental conditions, such as ambient temperature, also affect the phase and amplitude of a surface acoustic wave propagating through substance sensitive SAW device 14, reference SAW device 16 is included in chemical sensor 10 to compensate for these environmental effects. Reference SAW device 16 includes a feedback RF amplifier 34' having an output connected through a lead 36' to electrode 26 of the device, and an input connected through a lead 38' to electrode 18. Just as in substance sensitive SAW device 14, a surface acoustic wave is generated in reference SAW device 16 in the area of overlap between interlaced fingers 30 and 32, and propagates toward the region where interlaced fingers 22 and 24 are disposed at the other end of reference SAW device 16. A region 54 is disposed in the path of the surface acoustic wave, and may include a coating that has approximately the same mass as the coating in region 52, but unlike the polymer coating in region 52, the coating in region 54 does *not* absorb chemical substances. Thus, the mass of the coating in region 54 does *not* change when exposed to the chemical substance or substances which are absorbed in the coating applied to region 52.

Leads 36 and 36' are connected to a mixer 44, which produces an output signal corresponding to the difference in the frequency of the surface acoustic waves propagating within substance sensitive SAW device 14 and reference SAW device 16. Until the coating applied to region 52 in the substance sensitive SAW device 14 absorbs a chemical substance, the frequency of the surface acoustic waves input to mixer 44 from the two saw devices is approximately equal. However, once the coating applied to region 52 absorbs a chemical substance, the frequency of the surface acoustic waves propagating through region 52 changes relative to that of the surface acoustic waves propagating through region 54, due to the feedback loop. The differential between these two frequencies is determined by mixer 44 and supplied through a lead 46 to an amplifier 48. Amplifier 48 produces an amplified differential signal indicative of the shift in frequency or phase in the substance sensitive SAW device 14 due to exposure to the chemical substance of interest, enabling the substance (or at least a group of possible chemical substances) to be identified. The change in amplitude of the surface acoustic wave signal propagating through region 52 in chemical sensor 10 is *not* used, since the feedback RF amplifier is operating in a saturated region and thus, amplitude information is not available on lead 36.

As indicated in the Background of the Invention, a different chemical sensor 10 must be used for each chemical substance (or group of chemical substances to be detected). Moreover, to discriminate between related chemicals in a group of chemical substances of interest, different chemical sensors 10 are required, each having a different substance absorptive coating. Depending upon the number of substances to be identified, the multiplicity of chemical sensors may add an intolerable overhead to the cost of a chemical detection instrument.

Figure 2:
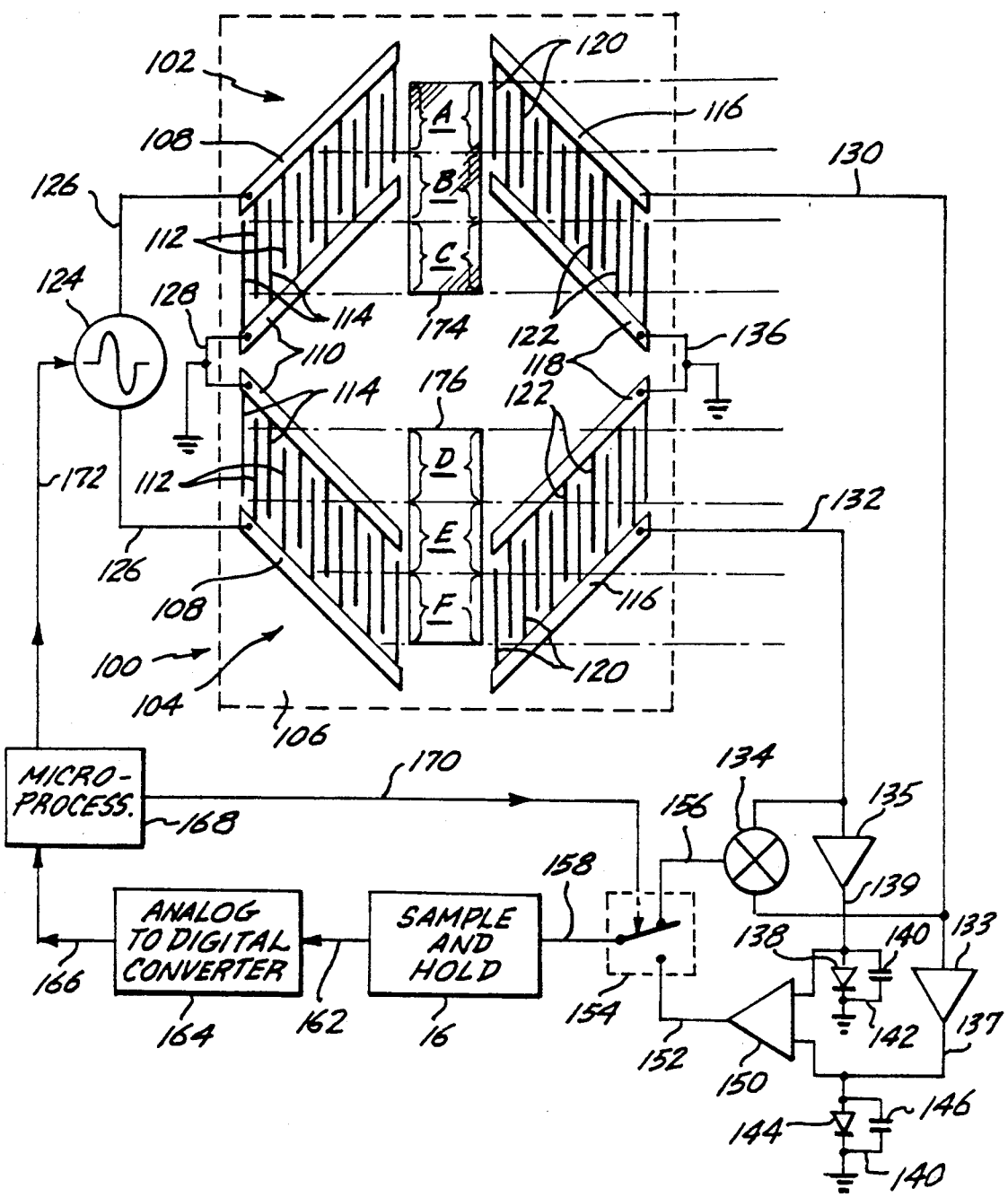
FIG. 2 is a schematic block diagram of a first embodiment of a SAW chemical sensor in accord with the present invention.

Accordingly, a chemical sensor 100 is shown in FIG. 2, which permits a plurality of different chemical substances to be detected as they are absorbed in a plurality of different coatings deposited on a common substrate 106 of the device. As in the prior art chemical sensor, both a substance sensitive SAW device 102 and a reference SAW device 104 are formed on common substrate 106. Both of the saw devices include inclined source electrodes 108 and 110 from which respectively extend interlaced fingers 112 and 114. Interlaced fingers 112 and 114 are substantially parallel to each other, but unlike those in prior art chemical sensor 10, the interlaced fingers in the present invention are not perpendicular to the electrodes from which they extend. Both the substance sensitive SAW device and reference SAW device also include inclined output electrodes 116 and 118, which are substantially parallel to each other, but are not parallel to inclined source electrodes 108 and 110. Interlaced fingers 120 and 122 extend inwardly from inclined output electrodes 116 and 118, respectively, are substantially parallel to each other and to interlaced fingers 112 and 114, but form an acute/obtuse angle with respect to inclined output electrodes 116 and 118. As a result of the inclined disposition of the source electrodes and output electrodes, successive interlaced fingers 112 and 114, and 120 and 122 overlap different regions in the area between inclined source electrodes 108 and 110 and inclined output electrodes 116 and 118.

In the preferred embodiment of chemical sensor 100 shown in FIG. 2, an area 174 between the electrodes is divided into three regions labeled A, B, and C with respect to substance sensitive SAW device 102, and an area 176 is divided into regions D, E and F with respect to reference SAW device 104. Region A lies between overlapped interlaced fingers 112 and 114 and 120 and 122, adjacent the proximal ends of inclined source electrodes 108 and 110 and inclined output electrodes 116 and 118. Region C lies between successive overlapped interlaced fingers 112/114 and 120/122, disposed at the distal ends of the inclined source and output electrodes. Intermediate region B lies between the overlapped interlaced fingers that are generally proximate the middle portion of the inclined source and output electrodes. Similarly, regions F, E and D in area 176 of the reference SAW device correspond to regions A, B and C, respectively, with respect to their disposition between overlapping successive interlaced fingers 112/114 and 120/122. (Alternating long and short dash lines extend between overlapped interlaced fingers 112/114 and 120/122 in FIG. 2 to clearly illustrate the regions associated therewith.) Each of regions A, B, and C in area 174 preferably comprise a different organic polymer coating selected for its characteristic absorption of a specific chemical substance or substances. Coatings comprising regions D, E, and F in area 176 are selected to substantially match the mass of the respective polymer coatings used in the corresponding regions of area 174, but as a general rule, do *not* absorb any chemical substances.

An impulse signal source 124 is connected through leads 126 to inclined source electrodes 108 in both the substance sensitive SAW device and the reference SAW device. Leads 128 connect inclined source electrodes 110 to ground. Leads 130 and 132 connect inclined output electrodes 116 of the substance sensitive SAW device and the reference device, respectively, to matched gain buffer amplifiers 133 and 135. These amplifiers isolate the signals on leads 130 and 132 from the signal at the output of buffer amplifiers 133 and 135 which are respectively connected through leads 137 and 139 to each input of a differential amplifier 150. Inclined output electrodes 118 of both devices are connected to ground through leads 136. Leads 130 and 132 also connect to a mixer 134, while leads 137 and 139 connect to the anodes of diodes 144 and 138, respectively. Capacitors 140 and 146 are connected in parallel with diodes 138 and 144, respectively, the cathode of each diode and one side of each capacitor being connected to ground by leads 142 and 148. The output of differential amplifier 150 is conveyed through a lead 152 to an electronic switch 154, comprising one of two contacts. The other contact is connected to the output of mixer 134 through a lead 156. From electronic switch 154, an output signal is conveyed through a lead 158 to a sample and hold circuit 160. A lead 162 connects the output of the sample and hold circuit to the input of an analog-to-digital converter 164, which produces a corresponding digital signal that is input to a microprocessor 168 over a lead 166. Microprocessor 168 is programmed to provide a select signal over a lead 170 that is connected to electronic switch 154, and is operative to control the switch so that it connects either the output from mixer 134 or the output from differential amplifier 150 to the input of sample and hold circuit 160. In addition, microprocessor 168 is programmed to control impulse signal source 124 via a timing control signal input to it over a lead 172.

OPERATION OF THE CHEMICAL SENSOR

Periodically, microprocessor 168 sends the timing control signal to impulse signal source 124, causing it to produce a periodically varying electrical pulse, which is applied to inclined source electrodes 108 on both substance sensitive SAW device 102 and reference SAW device 104. In response to the electrical pulse, the SAW devices generate surface acoustic wave packets in substrate 106 simultaneously across the entire length of the inclined output electrodes 116 and 118 in both devices. The acoustic wave packet propagates from left to right (relative to the view shown in FIG. 2) at a SAW velocity that is characteristic of the density of the materials coating the substrate. So long as the length of the overlapped portions of interlaced fingers 112/114 and 120/122 are many wavelengths of the surface acoustic waves, these waves propagate perpendicularly away from interlaced fingers 112 and 114, to be intercepted by the corresponding overlapped interlaced fingers 120 and 122. A portion of the surface acoustic wave generated by overlapped interlaced fingers 112 and 114 on the rightmost ends of inclined source electrodes 108 and 110 is intercepted first by the overlapped portions of interlaced fingers 120 and 122 on the proximal end (or left side, as shown) of inclined output electrodes 116 and 118. Likewise, the portion of the surface acoustic wave generated between successive overlapped portions of interlaced fingers 112 and 114 that are opposite regions B and E are intercepted by the overlapped portions of interlaced fingers 120 and 122 at a later point in time, and the surface acoustic wave passing through regions C and D are intercepted by overlapped interlaced fingers 120 and 122 at a still later point in time.

Figure 4:
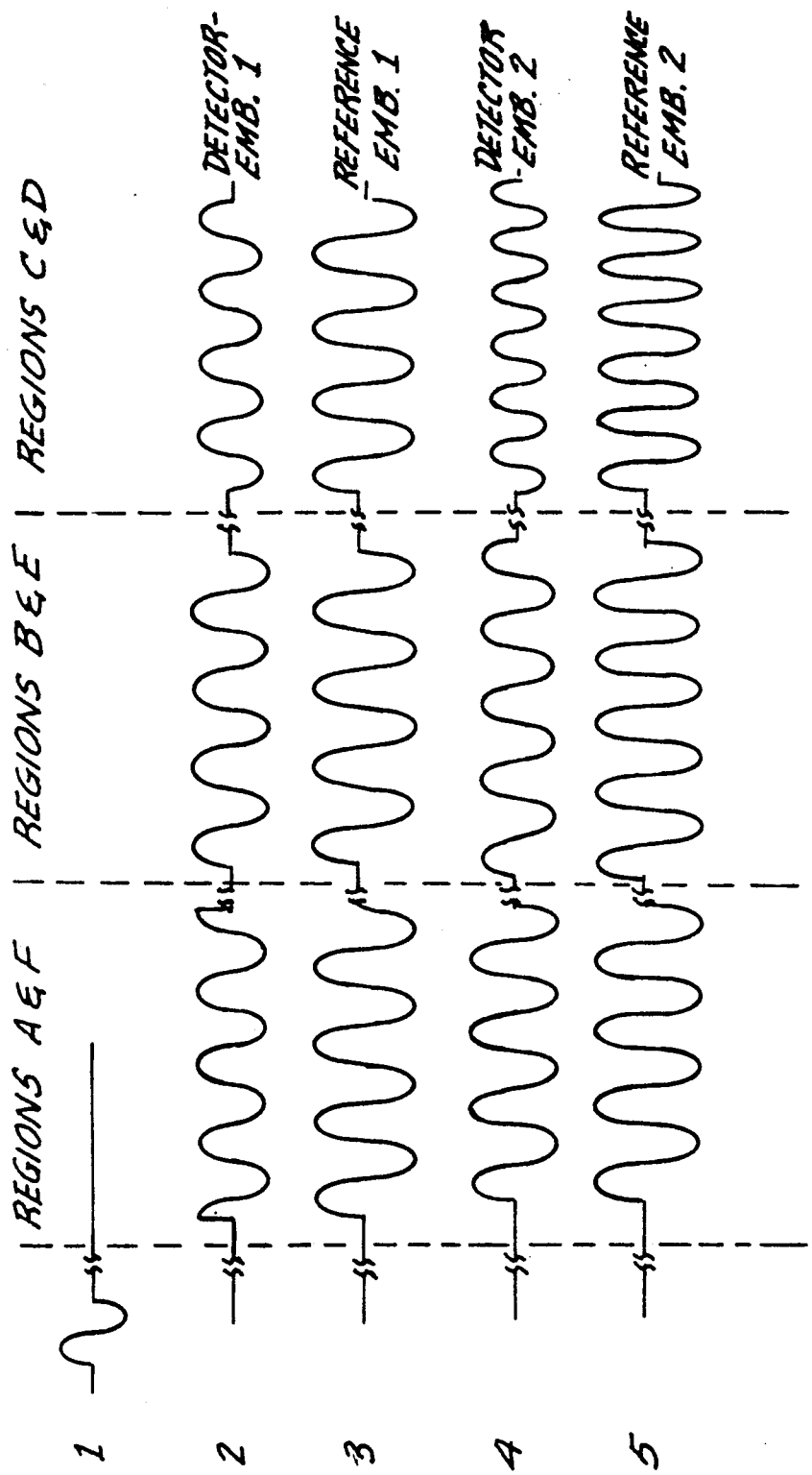
FIG. 4 graphically illustrates the relative phase and amplitude of signals in the two embodiments of the SAW chemical sensor, which are shown in FIGS. 2 and 3.

Turning now to FIG. 4, line 1 illustrates the pulse applied to the inclined source electrodes 108 and 110. In line 2 of FIG. 4, the signal developed on inclined output electrodes 116 and 118 is shown for each of regions A, B, and C. By comparison, the equivalent signals developed on inclined output electrodes 116 and 118 for reference SAW device 104 are shown in line 3 of the figure. From the comparison of phase and amplitude of the surface acoustic waves after they have passed through corresponding regions A and F, B and E, and C and D of the two SAW devices, it can be determined whether the polymeric coatings comprising regions A, B, and C have either absorbed different chemical substances, or have absorbed the same chemical substance in differing degrees. As a result of the absorption of the chemical substance or substances, the signals developed at inclined output electrodes 116 and 118 in substance sensitive SAW device 102 are different than the signals in reference SAW device 104, both in respect to phase and amplitude. For the particular examples in FIG. 4, region B (line 2) shows the least amount of change in these parameters, compared to the signal for the corresponding region E (line 3). As explained above, the surface acoustic waves propagating through regions A and F arrive at the inclined output electrodes before those propagating through regions B and E, and C and D. Accordingly, the signal present on leads 130 and 132 represents a time division multiplexed signal, for which the differential between the surface acoustic waves propagating through each of these three pairs of regions, A and F, B and E, and C and D are spaced apart in time and therefore, may be separately analyzed.

Microprocessor 168 initially causes electronic switch 154 to connect the output of mixer 134 to sample and hold circuit 160 to detect the differences in phase between the surface acoustic waves respectively propagating through regions A and F, then causes the electronic switch to connect the output of differential amplifier 150 to the sample and hold circuit to measure the relative amplitude difference of the two surface acoustic waves. Phase and amplitude differences are thus similarly successively measured for the surface acoustic waves passing through the other corresponding pairs of regions B and E, and C and D. These analog signals representing phase and amplitude differences are each input to sample and hold circuit 160 and are then converted to a digital value by A-to-D converter 164 for input to microprocessor 168.

Diodes 138 and 144, and capacitors 140 and 146 are provided at the input of differential amplifier 150 to half-wave filter the time multiplexed signals present on leads 130 and 132, so that the output of the differential amplifier corresponds to an average amplitude difference for the negative half cycle of the surface acoustic wave passing through each of the respective pairs of regions. The signal output from mixer 134 corresponds to the difference in phase of the negative half cycles of the surface acoustic waves passing through the respective pairs of regions. Microprocessor 168 sorts out the phase differences and amplitude differences for each of the regions based upon the time at which these signals are sampled, permitting identification of a particular chemical substance or substances with respect to the pattern of absorption of substance or substances in the polymer coatings applied to regions A, B and C. Since a particular substance or group of chemical substances absorbed into each of these coatings in regions A, B, and C, causes a characteristic change in the surface acoustic waves propagating through each region, the chemical substance or group of chemical substances can thus be identified by the effect on phase *and* amplitude for all of the regions by comparison against a set of known effects for chemical substance or substances of interest. Microprocessor 168 is programmed to compare the differential values for phase and amplitude of the surface acoustic waves propagating through each of the corresponding pairs of regions to this known set of values and thus to identify the chemical substance or substances that have caused the changes within substance sensitive SAW device 102 as compared to the unaffected surface acoustic waves propagating through reference SAW device 104. Any environmental effects, such as the effect of ambient temperature, are automatically compensated, since both the substance sensitive SAW device and reference SAW device are formed on the same substrate 106 and exposed to the same environmental conditions. Similarly, the effect of transducer orientation on the propagation characteristics of surface acoustic waves in substrate 106 are compensated, since both SAW devices are oriented on the common substrate so that interlaced fingers 112 and 114, and 120 and 122 on each of the devices are substantially parallel.

One problem that may arise in the first embodiment of chemical sensor 100 relates to the possible ambiguity in detecting differences in phase between the surface acoustic waves propagating through substance sensitive SAW device 102 and reference SAW device 104. If the substance absorbed by the polymer coating comprising one of the regions in area 174 causes more than one cycle of phase shift, ambiguity can occur in the signal output from mixer 134 for that region. A further potential problem relates to differences in sensitivity of the various polymer coatings applied to the regions on substance sensitive SAW device 102. Since the same SAW frequency is applied to the polymer coatings in each of these regions, a more sensitive polymer coating may detect a substance that it absorbs much more readily than a less sensitive coating that is selected for its affinity to absorb a different substance. Generally, less sensitive coating materials should be sampled with a higher frequency surface acoustic wave than more sensitive coating materials, since the response is generally greater with increased frequency.

Figure 3:
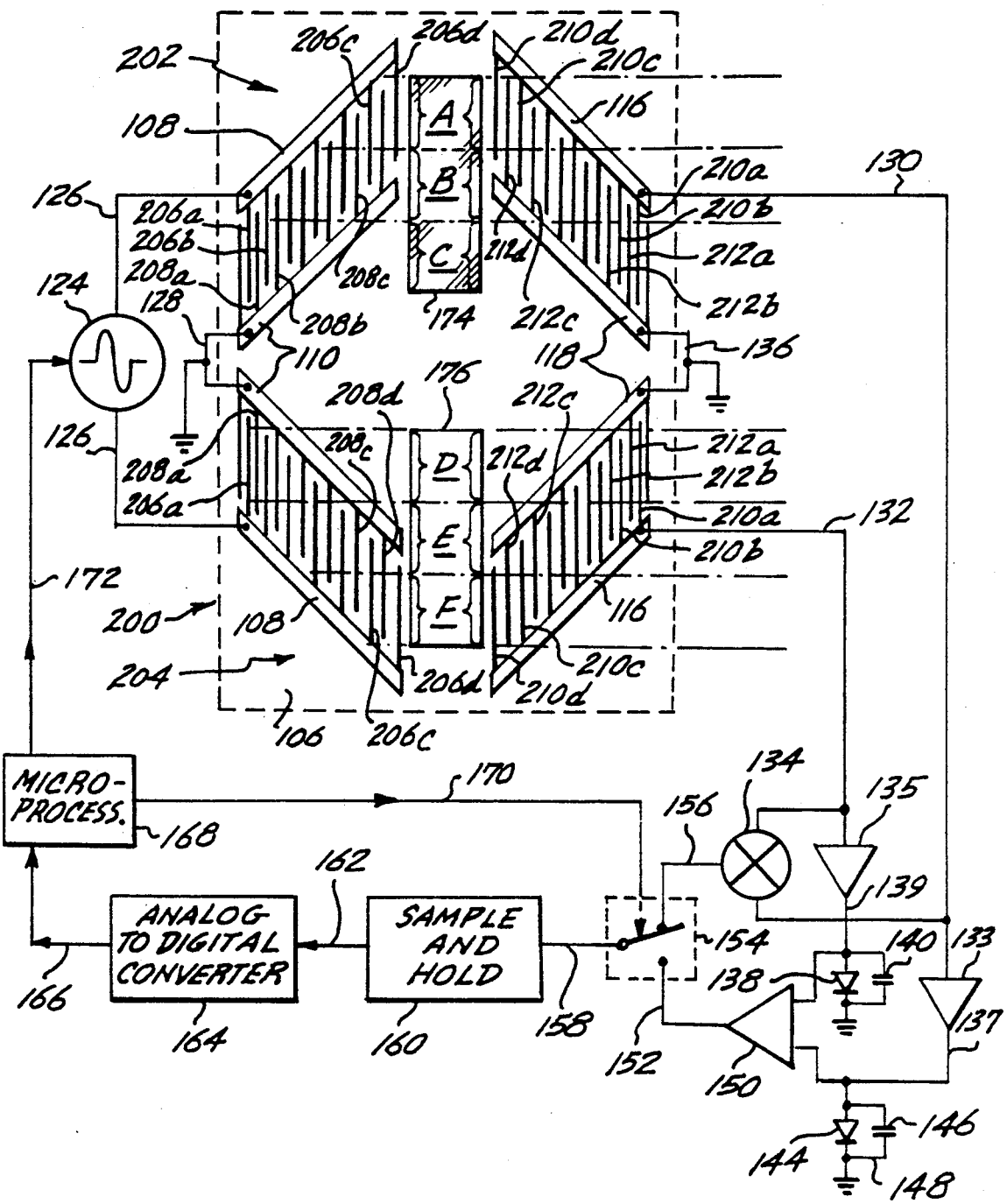
FIG. 3 is a schematic block diagram of a second embodiment of the SAW chemical sensor.

In consideration of these concerns, a second preferred embodiment of a chemical sensor 200 is shown in FIG. 3. To the extent that the same or equivalent components are used as in chemical sensor 100, the same reference numerals designate those components in both FIGS. 2 and 3. A primary difference between chemical sensors 100 and 200 relates to the disposition of interlaced fingers 206 and 208, and interlaced fingers 210 and 212. In both a substance sensitive SAW device 202 and a reference SAW device 204, interlaced fingers 206 and 208 extend outwardly of inclined source electrodes 108 and 110, respectively, substantially in parallel alignment with one another. Similarly, interlaced fingers 210 and 212 extend outwardly from inclined output electrodes 116 and 118, respectively, substantially in parallel alignment with each other and with interlaced fingers 206 and 208. However, adjacent interlaced fingers 206 and 208 and adjacent interlaced fingers 210 and 212, which are disposed proximate the distal ends of the inclined source electrodes and inclined output electrodes are spaced substantially closer together than are the interlaced fingers that are disposed at the proximal ends of the inclined source and output electrodes.

In FIG. 3, representative pairs of adjacent interlaced fingers 206a and 208a are disposed at the distal ends of inclined source electrodes 108 and 110, and are shown relatively closer together than a successive pair of adjacent interlaced fingers 206b and 208b. Between each successive pair of adjacent interlaced fingers along the length of the inclined source electrodes, the spacing becomes increasingly greater, reaching a maximum at the ends of the inclined source electrodes proximate the output electrodes, where the spacing between interlaced fingers 206d and 208d is a maximum. In the same manner, the spacing between interlaced fingers 210 and 212 is at a minimum between representative interlaced fingers 210a and 212a, which are disposed at the distal ends of the inclined output electrodes, reaching a maximum between adjacent and interlaced fingers 210d and 212d, disposed at the ends of the inclined output electrodes proximate the inclined source electrodes. Furthermore, the spacing between interlaced fingers 206d and 208d equals the spacing between interlaced fingers 210d and 212d, and the spacing between other corresponding adjacent pairs of the interlaced fingers 206 and 208 extending between the inclined source electrodes is equal to the spacing between other corresponding adjacent pairs of interlaced fingers 210 and 212, extending between the inclined output electrodes.

Thus, it will be apparent that the frequency of a surface acoustic wave generated by the overlapped portions of adjacent interlaced fingers of inclined source electrodes 108 and 110, for both substance sensitive SAW device 202 and reference SAW device 204, varies between the proximal and distal ends of inclined source electrodes 108 and 110 and inclined output electrodes 116 and 118. Moreover, the frequency of the surface acoustic waves propagating through regions A and F, which are disposed between the proximal ends of the inclined source and output electrodes, is substantially lower than the frequency of the surface acoustic waves propagating through regions C and D, disposed between the distal ends of those electrodes.

By applying a polymer coating to region C, which has a lower sensitivity to a specific chemical substance or substances as compared to the respective sensitivities of the polymer coatings applied to regions B and A, differences in the sensitivities of the polymer coatings are at least partially compensated. The lower frequency surface acoustic wave passing through region A tends to reduce its sensitivity to a chemical substance, while the higher frequency surface acoustic wave that propagates through region C increases its sensitivity to detect a specific chemical substance.

Under control of microprocessor 168, impulse signal source 124 supplies a periodically varying RF pulse to inclined source electrodes 108 having a frequency that is centered between the extreme upper and lower frequencies of the surface acoustic waves determined by the spacing between adjacent interlaced fingers 206a and 208a, and 206d and 208d. The surface acoustic waves received by inclined output electrodes 116 and 118 sweep through the frequency corresponding to the spacing between adjacent interlaced fingers 210a and 212a, and 210d and 212d. Since the sensitivity of the different coatings applied to the regions in area 174 is at least partially compensated by the variation in the frequency of the surface acoustic waves, the requirements for dynamic range in mixer 134 and in differential amplifier 150 are substantially reduced.

Line 1 of FIG. 4 illustrates the periodically varying RF pulse that is applied to the source electrodes. Lines 4 and 5 of this figure respectively illustrate the different frequencies of the surface acoustic wave propagating through the corresponding pairs of regions A and F, B and E, and C and D.

The output of mixer 134 is not constant for any given measurement interval corresponding to the receipt of the surface acoustic waves by inclined output electrodes 116 and 118, but instead, has a beat frequency proportional to the amount of detected substance absorbed by the polymer coating applied to any of regions A, B, and C. The beat frequency results because the absorption of a chemical substance by a region in area 174 causes a delay in the surface acoustic wave propagating through the region. The beat frequency of the signal output from mixer 134 thus becomes the measured parameter for delay and is not subject to phase cycle ambiguity as is the corresponding output in chemical sensor 100. In addition, differences in amplitude of the surface acoustic waves propagating through each of the corresponding pairs of regions A and F, B and E, and C and D determine the output of differential amplifier 150. This differential signal thus comprises a second parameter used to determine which substance or substances have been absorbed by the polymer coatings applied to regions A, B, and C, as explained above with respect to chemical sensor 100.

Although chemical sensors 100 and 200 have been disclosed as comprising only three regions to which a different polymer coating is applied for absorbing specific chemical substances, it should be apparent that additional regions may be applied to substrate 106, by extending the length of the inclined source and output electrodes, the limit to the possible number of such regions being determined by dimensional considerations, i.e., interlaced finger overlap length, width of the substance sensitive and reference SAW devices as measured between the distal ends of the inclined source and output electrodes, and the available size of substrate 106. The extent of overlap between the adjacent interlaced fingers determines the degree to which the surface acoustic waves propagating perpendicularly away from the interlaced fingers start to spread. Accordingly, the length of the overlapped interlaced fingers may be the ultimate limiting concern with respect to extending the length of the inclined source and output electrodes, so that the interlaced fingers overlap a large number of regions.

While the present invention has been disclosed with respect to preferred embodiments and modifications thereto, those of ordinary skill in the art will understand that further modifications may be made to the invention within the scope of the claims, which follow. Accordingly, it is not intended that scope of the invention be in anyway limited by the disclosure, but instead that it be determined entirely by reference to the claims.

The embodiments of the invention in which an exclusive property or privilege is claimed are defined as follows:

1. A surface acoustic wave sensor for detecting a substance, comprising
   (a) a first pair of electrodes formed on a surface of a substrate, said first pair of electrodes including a plurality of spaced apart, generally parallel interlaced fingers extending from one electrode of the first pair toward the other electrode of the first pair;
   (b) a second pair of electrodes formed on the surface of the substrate, spaced apart from the first pair of electrodes, one end of each of the second pair of electrodes being substantially closer to the first pair of electrodes than an opposite end thereof, said second pair of electrodes also including a plurality of spaced apart, interlaced fingers extending from one electrode of the second pair toward the other electrode of the second pair, generally parallel to each other and to the interlaced fingers of the first pair of electrodes, said first and second pairs of electrodes being disposed on the substrate so that the extent of overlap between any interlaced finger and successive interlaced fingers of the first and second electrode pairs varies along the length of individual electrodes of said electrode pairs; and
   (c) a plurality of different coatings disposed in regions on the substrate, in an area between the first pair of electrodes and the second pair of electrodes, said coatings changing the phase, delay, and amplitude of a surface acoustic wave propagating over the substrate generally transverse to and between the overlapping interlaced fingers of the first and second pair of electrodes and similarly affecting a signal output from the second pair of electrodes in response thereto, as a function of the amount of the substance absorbed by the coating of the region through which the surface acoustic wave passes.

2. The surface acoustic wave sensor of claim 1, wherein the spacing between successive adjacent interlaced fingers is substantially constant for both the first pair of electrodes and the second pair of electrodes.

3. The surface acoustic wave sensor of claim 1, wherein ends of said electrode pairs that are closer are proximal ends, and ends of said electrode pairs that are farther apart are distal ends, and wherein the spacing between successive adjacent interlaced fingers, for both the first pair of electrodes and the second pair of electrodes, varies from their proximal ends to their distal ends, so that the frequency of the surface acoustic wave propagating over the substrate varies between the proximal and distal ends of the first and second pair of electrodes, the frequency of the output signal being delayed in time as a function of the amount of the substance absorbed by the coating of the region through which the surface acoustic wave propagates.

4. The surface acoustic wave sensor of claim 3, wherein the spacing between the adjacent interlaced fingers is greater at the proximal ends of the first and second pair of electrodes than at their distal ends, so that a coating that is disposed between interlaced fingers extending from the proximal ends of the first and second pair of electrodes is exposed to a lower frequency surface acoustic wave than is a coating that is disposed between interlaced fingers extending from the distal ends of the first and second pair of electrodes.

5. The surface acoustic wave sensor of claim 1, further comprising a reference surface acoustic wave device including:
   (a) a third pair of electrodes formed on a surface of the substrate, said third pair of electrodes including a plurality of spaced apart, generally parallel interlaced fingers extending from one electrode of the third pair toward the other electrode of the third pair;
   (b) a fourth pair of electrodes formed on the surface of the substrate, spaced apart from the third pair of electrodes, one end of each of the fourth pair of electrodes being substantially closer to the third pair of electrodes than an opposite end thereof, said fourth pair of electrodes also including a plurality of spaced apart, interlaced fingers extending from one electrode of the fourth pair toward the other electrode of the fourth pair, substantially parallel to each other and to the interlaced fingers of the third pair of electrodes, said third and fourth pairs of electrodes being disposed on the substrate so that the extent of overlap between any interlaced finger and successive interlaced fingers of the third and fourth electrode pairs varies along the length of individual electrodes of said electrode pairs; and (c) a chemically nonabsorptive coating disposed on the substrate, in an area between the third pair of electrodes and the fourth pair of electrodes, said nonabsorptive coating being substantially unaffected by the substances absorbed by the coatings between the first and second pair of electrodes, so that the phase and amplitude of a surface acoustic wave propagating over the substrate between overlapping interlaced fingers of the third and fourth pairs of electrodes are not affected by such substances.

6. The surface acoustic wave sensor of claim 5, wherein the reference surface acoustic wave device provides a reference signal for comparison to the signal output from the second pair of electrodes to compensate said signal for temperature effects.

7. The surface acoustic wave sensor of claim 5, wherein the interlaced fingers of the third and fourth pair of electrodes are generally aligned with the interlaced fingers of the first and second pair of electrodes, respectively, said reference surface acoustic wave device thereby being operative to minimize the effect on the surface acoustic wave sensor of the orientation of the first and second pair of electrodes with respect to the substrate.

8. The surface acoustic wave sensor of claim 1, further comprising impulse signal means, connected to apply a periodically varying voltage signal to the first pair of electrodes to excite the surface acoustic wave.

9. The surface acoustic wave sensor of claim 1, further comprising analysis means connected to receive the signal output from the second pair of electrodes for monitoring the change in amplitude and either a phase shift or a delay of the surface acoustic wave caused by the absorption of a substance by any of the plurality of coatings.

10. The surface acoustic wave sensor of claim 9, further comprising a reference surface acoustic wave device disposed on the substrate, through which a reference surface acoustic wave propagates, said analysis means being further operative to compare a signal output from the reference surface acoustic wave device to a signal output from the second pair of electrodes to determine changes in the amplitude and either the phase shift of delay of the surface acoustic wave caused by the substance with respect to the reference surface acoustic wave, said reference acoustic wave being unaffected by the substance.

11. A sensor for identifying a plurality of substances, comprising:

(a) first surface acoustic wave transducer means, having two pairs of inclined electrodes and a plurality of coatings disposed between the pairs of inclined electrodes, each coating being absorptive of one specific substance of the plurality of substances available, for providing a sensor signal indicative of a surface acoustic wave propagating through the coatings generally transverse to and between the pairs of inclined electrodes, wherein the sensor signal varies in phase and amplitude as a function of the amount of each of the plurality of substances absorbed by the coatings;

(b) second surface acoustic wave transducer means, having two pairs of inclined reference electrodes and a chemically nonabsorptive coating disposed between the pairs of inclined reference electrodes, for providing a reference signal indicative of a surface acoustic wave propagating through the chemically nonabsorptive coating;

(c) impulse means for generating a periodically varying signal that is applied to both the first and the second surface acoustic wave transducer means to create the surface acoustic waves propagating therethrough; and (d) signal processing means, for determining a change in the sensor signal relative to the reference signal due to absorption of any of the plurality of substances into the coatings, characteristic changes thereof being used to identify a specific one of the substances to which the sensor is exposed.

12. The sensor of claim 11, wherein only a portion of the surface acoustic wave in the first surface acoustic transducer means propagates from one pair of inclined electrodes through each of the plurality of coatings that are disposed between the two pairs of electrodes of said first surface acoustic wave transducer means, and wherein the first surface acoustic wave transducer means include a plurality of interdigital electrodes extending from the inclined electrodes in spaced apart parallel array, the portion of the surface acoustic wave that propagates through each of the plurality of coatings lying transverse to an area of overlap between adjacent interdigital electrodes.

13. The sensor of claim 12, wherein the spacing between adjacent interdigital electrodes is constant along the length of the electrodes.

14. The sensor of claim 12, wherein the spacing between adjacent interdigital electrodes varies along the length of the electrodes, causing the frequency of the surface acoustic wave propagating through the coatings between the electrodes of the first surface acoustic wave transducer means to vary along the length of the electrodes and at the plurality of coatings.

15. The sensor of claim 11, wherein the signal processor means are further operative to determine time multiplexed changes in phase and amplitude between the sense signal and the reference signal so the time multiplexed changes can be attributed to a specific one of the coatings, and further operative to identify the specific substance by comparing the time multiplexed changes to a set of known time multiplexed changes, each of the known time multiplexed changes of the set corresponding to a specific chemical substance.

16. A method for sensing and identifying one or more of a plurality of different substances, comprising the steps of:

(a) generating a first surface acoustic wave;

(b) propagating the acoustic wave through a plurality of coatings, each coating being selected to absorb one specific substance of the plurality of substances available, so that the first surface acoustic wave passes through each coating at different times, producing a time dependent sense signal;

(c) generating a second surface acoustic wave that comprises a time dependent reference signal;

(d) determining a change between the time dependent sense signal and the time dependent reference signal due to absorption of any of the plurality of the substances into the plurality of coatings; and (e) identifying a substance absorbed by one or more of the plurality of coatings as a function of the change of the time dependent sense signal caused by such absorption.

17. The method of claim 16, wherein the plurality of coatings comprise a plurality of regions disposed between inclined electrodes of a surface acoustic wave transducer, a portion of the first surface acoustic wave propagating through a region lying closer to overlapping areas of the electrodes than regions more remotely disposed therefrom.

18. The method of claim 16, wherein the steps of generating the first and second surface acoustic waves comprise the step of producing a pulse having a time varying amplitude that is applied to excite the first and second surface acoustic waves in a first and in a second surface acoustic wave transducer.

19. The method of claim 16, wherein the first and the second surface acoustic waves both vary in frequency over time as a result of variations in the separation between adjacent inclined electrodes used to produce said surface acoustic waves.

20. The method of claim 19, wherein the plurality of coatings have different sensitivities to the specific one of the plurality of substances that they are selected to detect; and wherein the step of propagating includes the steps of ordering the disposition of the coatings between the inclined electrodes as a function of their sensitivity, and propagating a higher frequency portion of the first surface acoustic wave through one or more of the plurality of coatings having a relatively lower sensitivity.

21. The method of claim 19, further comprising the step of compensating for a phase shift ambiguity by determining a delay in the sense signal, relative to the reference signal, measured as a beat frequency.

* * * * *